US011555817B2

(12) United States Patent
Petty

(10) Patent No.: US 11,555,817 B2
(45) Date of Patent: Jan. 17, 2023

(54) BIOMARKER RATIO IMAGING MICROSCOPY

(71) Applicant: The Regents of the University of Michigan, Ann Arbor, MI (US)

(72) Inventor: Howard R. Petty, Livonia, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/305,343

(22) PCT Filed: May 31, 2017

(86) PCT No.: PCT/US2017/035253
§ 371 (c)(1),
(2) Date: Nov. 28, 2018

(87) PCT Pub. No.: WO2017/210322
PCT Pub. Date: Dec. 7, 2017

(65) Prior Publication Data
US 2020/0319187 A1    Oct. 8, 2020

Related U.S. Application Data

(60) Provisional application No. 62/343,464, filed on May 31, 2016.

(51) Int. Cl.
*G01N 33/574* (2006.01)
*G01N 21/64* (2006.01)
*G16B 40/00* (2019.01)
*G16B 20/00* (2019.01)

(52) U.S. Cl.
CPC ... *G01N 33/57415* (2013.01); *G01N 21/6458* (2013.01); *G01N 33/57492* (2013.01); *G16B 20/00* (2019.02); *G16B 40/00* (2019.02)

(58) Field of Classification Search
CPC combination set(s) only.
See application file for complete search history.

(56) References Cited

U.S. PATENT DOCUMENTS

| 6,055,325 | A | * | 4/2000 | Garini | G06V 10/88 382/129 |
| 2005/0142573 | A1 | | 6/2005 | Glinski | |
| 2013/0059903 | A1 | * | 3/2013 | Raman | C12N 5/0695 514/44 A |
| 2013/0259858 | A1 | | 10/2013 | Zacksenhaus et al. | |
| 2015/0140124 | A1 | | 5/2015 | Lancaster et al. | |

OTHER PUBLICATIONS

Combs, C.A. ((2010), Fluorescence Microscopy: A Concise Guide to Current Imaging Methods. Current Protocols in Neuroscience, 50: 2.1.1-2.1.14).*
Sanderson et al (Cold Spring Harb Protoc. Oct. 2014; 2014(10): pdb.top071795).*
Perrone et al (PLoS ONE, 2012, 7:e43110, internet pp. 1-9).*
Robertson et al (Journal of Biomolecular Screening. 2010;15(7):820-829).*
Lee et al (Nanoscale, 2012, 4:124-129).*
breastcancer.org published Nov. 17, 2015 (https://www.breastcancer.org/research-news/mammograms-find-dcis-better-as-women-age).*
Currie et al (Human Pathology, 2013, 44:402-411).*
Al-Hajj et al., Prospective identification of tumorigenic breast cancer cells. Proc Natl Acad Sci USA. Apr. 1, 2003;100(7):3983-8.
Ashman et al., Detecting bimodality in astronomical datasets. Astronomical J. 1994;108:2348-61.
Axelrod. Fluorescence polarization microscopy. Methods Cell Biol. 1989;30:333-52.
Azimi et al., Altered purinergic receptor-$Ca^{2+}$signaling associated with hypoxia-induced epithelial-mesenchymal transition in breast cancer cells. Mol Oncol. Jan. 2016;10(1):166-78.
Bhowmick et al., fibroblasts in cancer initiation and progression. Nature. Nov. 18, 2004;432(7015):332-7.
Bleyer et al., Effect of three decades of screening mammography on breast-cancer incidence. N Engl J Med. Nov. 22, 2012;367(21):1998-2005.
Bright et al., Fluorescence ratio imaging microscopy. Methods Cell Biol. 1989;30:157-9.
Clark et al., Calicum microdomains form within neutrophils at the neutrophil-tumor cell synapse: role in antibody-dependent target cell apoptosis. Cancer Immunol Immunother. Jan. 2010;59(1):149-59.
Clark et al., Observation of calcium microdomains at the uropod of living morphologically polarized human neutrophils using flash lamp-based fluorescence microscopy. Cytometry A 73, 673-8 (2008).
Clark et al., Protocol for Biomarker Ratio Imaging Microscopy with Specific Application to Ductal Carcinoma In situ of the Breast. Front Cell Dev Biol. Nov. 3, 2016;4:120.
Currie et al., Immunohistochemical analysis of cancer stem cell markers in invasive breast carcinoma and associated ductal carcinoma in situ: relationships with markers of tumor hypoxia and microvascularity. Hum Pathol. Mar. 2013;44(3):402-11.
Donàet al., Directional tissue migration through a self-generated chemokine gradient. Nature. Nov. 14, 2013;503(7475):285-9.
Esserman et al., Overdiagnosis and overtreatment in cancer: An opportunity for improvement. JAMA. Aug. 28, 2013;310(8):797-8.
Exbrayat, J-M, ed. Histochemical and Cytochemical Methods of Visualization. CRC Press, Boca Raton, FL, pa. 299 (2013).
Floto et al., IgG-induced Ca2+ oscillations in differentiated U937 cells; a study using laser scanning confocal microscopy and co-loaded fluo-3 and fura-red fluorescent probes. Cell Calcium. Nov. 1995;18(5):377-89.
Gomez et al., Filopodial calcium transients promote substrate-dependent growth cone turning. Science. Mar. 9, 2001;291(5510):1983-7.

(Continued)

*Primary Examiner* — Laura B Goddard
(74) *Attorney, Agent, or Firm* — Casimir Jones SC; David W. Staple

(57) ABSTRACT

Provided herein are methods and systems for the analysis of biomarkers, and methods of providing diagnoses and/or prognoses therewith. In particular, methods and systems for performing biomarker ratio imaging microscopy (BRIM) are provided, as well as methods of using BRIM for the analysis of biomarker pairs (e.g., CD44/CD24, N-cadherin/E-cadherin, CD74/CD59, etc.) diagnosis and/or prognosis of cancer (e.g., ductal carcinoma in situ).

16 Claims, 10 Drawing Sheets

(56) References Cited

OTHER PUBLICATIONS

Harding et al., Breast cancer screening, incidence, and mortality across US counties. JJAMA Intern Med. Sep. 2015;175(9):1483-9.
Herrera-Gayol et al., Adhesion proteins in the biology of breast cancer: contribution of CD44. Exp Mol Pathol. Jun. 1999;66(2):149-56.
LEDFORD. Cancer theory faces doubts. Nature. Apr. 21, 2011;472(7343):273.
Li et al., Intrinsic resistance of tumorigenic breast cancer cells to chemotherapy. J Natl Cancer Inst. May 7, 2008;100(9):672-9.
Madjd et al., Loss of CD59 expression in breast tumours correlates with poor survival. J Pathol. Aug. 2003;200(5):633-9.
Mani et al., The epithelial-mesenchymal transition generates cells with properties of stem cells. Cell. May 16, 2008;133(4):704-15.
Marshall. Breast cancer. Dare to do less. Science. Mar. 28, 2014;343(6178):1454-6.
Metodieva et al., CD74-dependent deregulation of the tumor suppressor scribble in human epithelial and breast cancer cells. Neoplasia. Jun. 2013;15(6):660-8.
Moynihan et al., PPreventing overdiagnosis: how to stop harming the healthy. BMJ. May 28, 2012;344:e3502.
Nalbant et al., Activation of endogenous Cdc42 visualized in living cells. Science. Sep. 10, 2004;305(5690):1615-9.
Orimo et al., Stromal fibroblasts in cancer: A novel tumor-promoting cell type. Cell Cycle. Aug. 2006;5(15):1597-601.
Otsu. A threshold selection method from gray-level histograms. IEEE Trans. Sys. Man. Cyber. 9, 62-66 (1979).
Ozanne et al., Characterizing the impact of 25 years of DCIS treatment. Breast Cancer Res Treat. Aug. 2011;129(1):165-7.
Park et al., Combinatorial TGF-β attenuation with paclitaxel inhibits the epithelial-to-mesenchymal transition and breast cancer stem-like cells. Oncotarget. Nov. 10, 2015;6(35):37526-43.
Petty. Fluorescence microscopy: established and emerging methods, experimental strategies, and applications in immunology. Microsc Res Tech. Aug. 2007;70(8):687-709.
Porter et al., Molecular markers in ductal carcinoma in situ of the breast. Mol Cancer Res. Mar. 2003;1(5):362-75.
Shi et al., Identification of cancer stem cell-like cells from human epithelial ovarian carcinoma cell line. Cell Mol Life Sci. Nov. 2010;67(22):3915-25.
Singh et al., EMT, cancer stem cells and drug resistance: an emerging axis of evil in the war on cancer. Oncogene. Aug. 26, 2010;29(34):4741-51.
Wei et al., Calcium flickers steer cell migration. Nature. Feb. 12, 2009;457(7231):901-5.
Weigel et al., Digital Mammography screening: Does age influence the detection rates of low-, intermediate-, and high-grade ductal carcinoma in situ? Radiology. Mar. 2016;278(3):707-13.
International Search Report and Written Opinion for PCT/US2017/035253, dated Aug. 22, 2017, 12 pages.
Extended EP Search Report for EP17807414.2., dated Jun. 26, 2020, 10 pages.

\* cited by examiner

BIOMARKER RATIO IMAGING MICROSCOPY

CROSS-REFERENCE TO RELATED APPLICATION

The present application claims priority to U.S. Provisional Patent Application Ser. No. 62/343,464 filed May 31, 2016, which is hereby incorporated by reference in its entirety.

FIELD

Provided herein are methods and systems for the analysis of biomarkers, and methods of providing diagnoses and/or prognoses therewith. In particular, methods and systems for performing biomarker ratio imaging microscopy (BRIM) are provided, as well as methods of using BRIM for the analysis of biomarker pairs (e.g., CD44/CD24, N-cadherin/E-cadherin, CD74/CD59, etc.) for diagnosis and/or prognosis of cancer (e.g., ductal carcinoma in situ).

BACKGROUND

Ductal carcinoma in situ (DCIS) of the breast is the most common type of non-invasive breast cancer. In DCIS, epithelial cells proliferate within ducts, which are surrounded by a double layer of myoepithelial cells and basement membranes. Although it is believed that DCIS lesions become invasive breast cancer, this has not been proven, nor has the fraction of DCIS cases progressing to invasive cancer been established. The introduction of mammography led to a sharp increase in the number of DCIS cases. This increase, however, was not accompanied by a commensurate reduction in the number of advanced breast cancer patients. Several studies indicate that patients with insignificant disease are being treated (refs. 1-5; incorporated by reference in their entireties), which indicates the existence of both non-aggressive and aggressive forms of DCIS. It is not possible to stratify DCIS lesions according to aggressiveness, using existing techniques, with a precision sufficient to provide prognostic insight in patient care.

SUMMARY

Provided herein are methods and systems for the analysis of biomarkers, and methods of providing diagnoses and/or prognoses therewith. In particular, methods and systems for performing biomarker ratio imaging microscopy (BRIM) are provided, as well as methods of using BRIM for the analysis of biomarker pairs (e.g., CD44/CD24, N-cadherin/E-cadherin, CD74/CD59, etc.) for diagnosis and/or prognosis of cancer (e.g., ductal carcinoma in situ).

In some embodiments, provided herein are methods of evaluating a condition of a subject comprising: (a) quantitating a positively-correlated biomarker in a sample from the subject; (b) quantitating a negatively-correlated biomarker in a sample from the subject; (c) determining: (i) a ratio of the positively-correlated biomarker to the negatively-correlated biomarker, wherein the subject exhibits or is at risk of the condition if the ratio is above a threshold level, or (ii) a ratio of the negatively-correlated biomarker to the positively-correlated biomarker, wherein the exhibits or is at risk of the condition if the ratio is below a threshold level. In some embodiments, the condition is an invasive or aggressive form of cancer. In some embodiments, the subject previously tested positive for an abnormality, pre-cancer, or cancer during a screening. In some embodiments, the subject has tested positive for ductal carcinoma in situ (DCIS) and the condition being evaluated is invasive ductal carcinoma. In some embodiments, the biomarkers are plasma membrane proteins. In some embodiments, the positively-correlated biomarker is CD44 and the negatively-correlated biomarker is CD24. In some embodiments, the positively-correlated biomarker is CD74 and the negatively-correlated biomarker is CD59. In some embodiments, the positively-correlated biomarker is N-cadherin and the negatively-correlated biomarker is E-cadherin. In some embodiments, biomarker levels are quantitated by imaging microscopy. In some embodiments, each biomarker to be quantitated is labeled with a separately optically-detectable label. In some embodiments, the optically-detectable labels are fluorescent dyes. In some embodiments, the fluorescent dyes are conjugated to antibodies. In some embodiments, the antibodies are primary antibodies. In some embodiments, the fluorescent dyes are conjugated to secondary antibodies.

In some embodiments, provided herein are methods of stratifying the aggressiveness of ductal carcinoma in situ (DCIS) from a subject comprising: (a) exposing a sample from the subject to a first detection reagent which specifically binds to a first biomarker which is positively correlated with aggressive cancer; (b) exposing a sample from the subject to a second detection reagent which specifically binds to a second biomarker which is negatively correlated with aggressive cancer; (c) quantitating the level of the first and second biomarkers by detecting the first and second detection reagents using fluorescence imaging microscopy; and (d) generating (i) a ratio of the first biomarker to the second biomarker, wherein the subject exhibits or is at risk of aggressive cancer if the ratio is above a threshold level, or (ii) a ratio of the second biomarker to the first biomarker, wherein the exhibits or is at risk of aggressive cancer if the ratio is below a threshold level. In some embodiments, the sample is tissue from a biopsy. In some embodiments, DCIS was diagnosed by mammography. In some embodiments, the detection reagents are antibodies or antibody fragments. In some embodiments, the detection reagents are detected by binding labeled secondary antibodies to the detection reagents. In some embodiments, the first biomarker is positively correlated with invasive ductal carcinoma (IDC) and/or negatively correlated with fibroadenoma; and wherein the second biomarker is positively correlated with fibroadenoma and/or negatively correlated with IDC. In some embodiments, the subject exhibits or is at risk of IDC if the ratio is above/below a threshold level, or exhibits or is at risk of aggressive cancer if the ratio is below/above a threshold level.

DEFINITIONS

Figure 1:
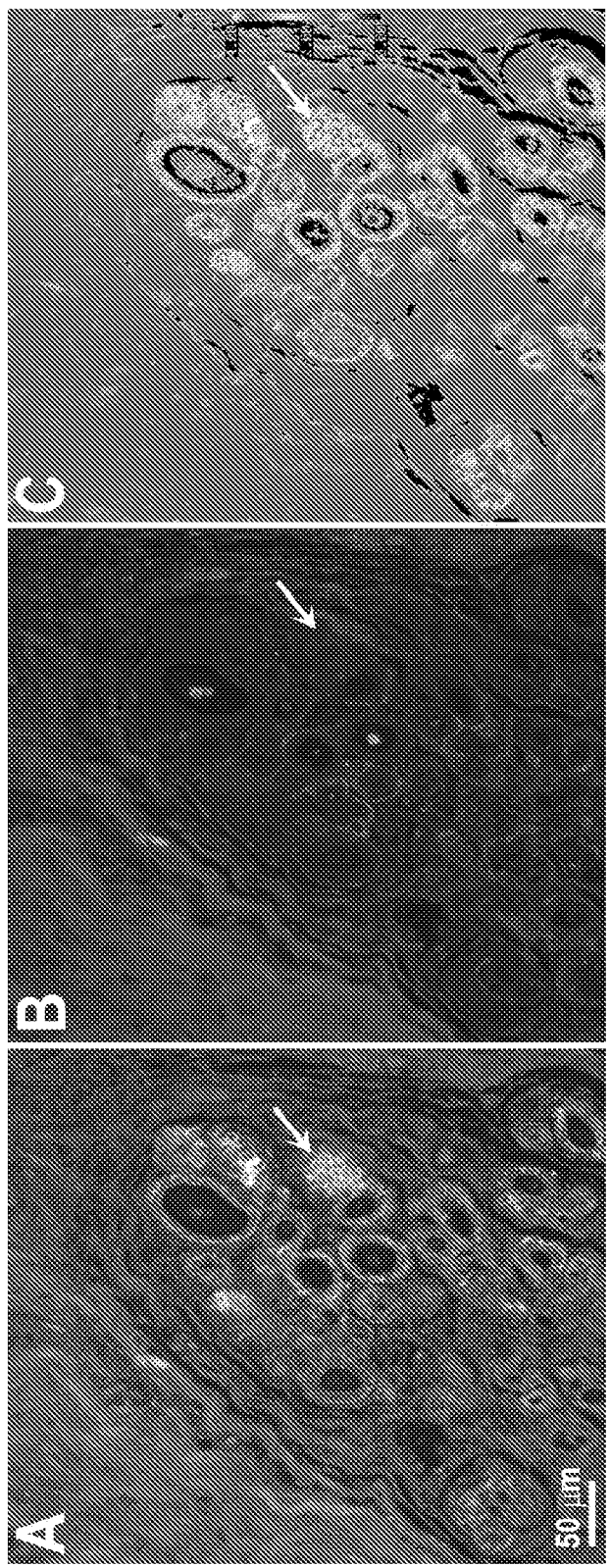
FIG. 1. Illustration of BRIM. A DCIS section was labeled with anti-CD44 (A) and anti-CD24 (B). Panels A and B were prepared identically. Panel C reveals intraductal $CD44^{hi}/CD24^{lo}$ cells at high contrast. The white arrows identify a region of $CD44^{hi}/CD24^{lo}$ cells that are included in the quantitative line profile analyses of panels D-F. Panels D-F show quantitative line profile analyses (the line profile extends from the right to left hand sides of the image at the level of the arrow). Noise reduction and contrast enhancement are seen in the ratio image of panel F. The image in panel C is scaled as indicated by the bar on the right side. Distance scale range is shown on the lower left side of panel A.
Figure 1:
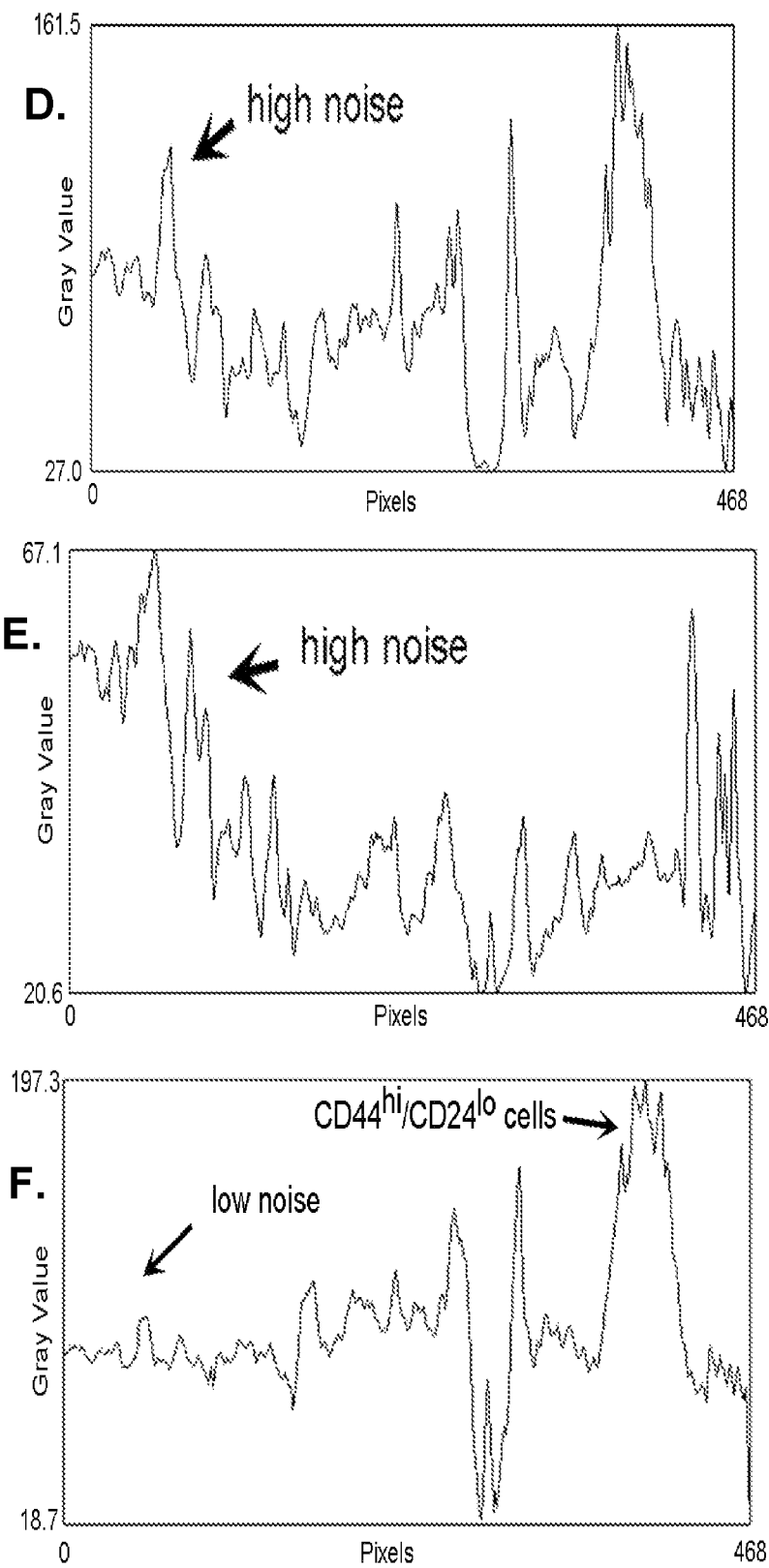

The terminology used herein is for the purpose of describing the particular embodiments only, and is not intended to limit the scope of the embodiments described herein. Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a biomarker ratio" is a reference to one or more biomarker ratios and equivalents thereof known to those skilled in the art, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a human subject that is being treated or evaluated for a disease or condition.

As used herein, the term "subject at risk for a disease," for example, "a subject at risk for cancer" refers to a subject with one or more risk factors for developing the disease (e.g., cancer). Depending upon the specific disease, risk factors may include, but are not limited to, gender, age, genetic predisposition, environmental exposures, infections, and previous incidents of diseases, lifestyle, etc.

As used herein, the term "sample" refers to any material, biological fluid, tissue, or cell obtained or otherwise derived from a subject. This includes blood (e.g., whole blood, leukocytes, peripheral blood mononuclear cells, buffy coat, plasma, and serum), sputum, tears, mucus, nasal washes, nasal aspirate, breath, urine, semen, saliva, peritoneal washings, ascites, cystic fluid, meningeal fluid, amniotic fluid, glandular fluid, lymph fluid, nipple aspirate, bronchial aspirate, bronchial brushing, synovial fluid, joint aspirate, organ secretions, cells, a cellular extract, and cerebrospinal fluid. This also includes experimentally separated fractions of all of the preceding. For example, a blood sample can be fractionated into serum, plasma, or into fractions containing particular types of blood cells, such as red blood cells or white blood cells (leukocytes). In some embodiments, a sample can be a combination of samples from an individual, such as a combination of a tissue and fluid sample. The term "sample" may also include materials containing homogenized solid material, such as from a stool sample, a tissue sample, or a tissue biopsy; and materials derived from a tissue culture or a cell culture. Any suitable methods for obtaining a sample can be employed; exemplary methods include, e.g., phlebotomy, swab, and a fine needle aspirate biopsy procedure. Exemplary tissues susceptible to fine needle aspiration include lymph node, lung, lung washes, BAL (bronchoalveolar lavage), thyroid, breast, pancreas, and liver. Samples can also be collected, e.g., by micro dissection, bladder wash, smear, or ductal lavage. A sample obtained or derived from an individual includes any such sample that has been processed in any suitable manner (e.g., filtered, diluted, pooled, fractionated, concentrated, etc.) after being obtained from the individual.

As used herein, "biomarker level" and "level" refer to a measurement that is made using any analytical method for detecting the biomarker in a biological sample and that indicates the presence, absence, absolute amount or concentration, relative amount or concentration, titer, a level, an expression level, a ratio of measured levels, or the like, of, for, or corresponding to the biomarker in the biological sample. The exact nature of the "level" depends on the specific design and components of the particular analytical method employed to detect the biomarker.

A "control level" of a target molecule refers to the level of the target molecule (or a ratio of levels) in the same sample type from an individual that does not have the disease or condition. A "control level" of a target molecule (or ratio of target molecules) need not be determined each time the present methods are carried out, and may be a previously determined level that is used as a reference or threshold to determine whether the level in a particular sample is higher or lower than a normal level. In some embodiments, a control level in a method described herein is the level that has been observed in one or more control subjects (e.g., subjects that have nonaggressive cancers or no cancer). In some embodiments, a control level in a method described herein is the average or mean level, optionally plus or minus a statistical variation that has been observed in a plurality of control subjects (e.g., subjects that have nonaggressive cancers or no cancer).

A "threshold level" of a target molecule (or a ratio of target molecules) refers to the level beyond which (e.g., above or below, depending upon the biomarker(s)) is indicative of or diagnostic for a particular disease, condition, or prognosis (e.g., aggressive form of cancer). A "threshold level" of a target molecule (or a ratio of target molecules) need not be determined each time the present methods are carried out, and may be a previously determined level that is used as a reference or threshold to determine whether the level in a particular sample is higher or lower than a normal level. In some embodiments, a subject with a biomarker level beyond (e.g., above or below, depending upon the biomarker(s)) a threshold level has a statistically significant likelihood (e.g., 80% confidence, 85% confidence, 90% confidence, 95% confidence, 98% confidence, 99% confidence, 99.9% confidence, etc.) of, for example, having or developing an aggressive form of cancer.

"Diagnose", "diagnosing", "diagnosis", and variations thereof refer to the detection, determination, or recognition of a health status or condition of an individual on the basis of one or more signs, symptoms, data, or other information pertaining to that individual. The health status of an individual can be diagnosed as healthy/normal (e.g., a diagnosis of the absence of a disease or condition, diagnosis of a non-aggressive form of cancer, etc.) or diagnosed as ill/abnormal (e.g., a diagnosis of the presence, or an assessment of the characteristics, of a disease or condition, diagnosis of a non-aggressive form of cancer, etc.). The terms "diagnose", "diagnosing", "diagnosis", etc., encompass, with respect to a particular disease or condition, the initial detection of the disease; the characterization or classification of the disease; the detection of the progression, remission, or recurrence of the disease; and the detection of disease response after the administration of a treatment or therapy to the individual.

"Prognose", "prognosing", "prognosis", and variations thereof refer to the prediction of a future course of a disease or condition in an individual who has the disease or condition (e.g., predicting patient survival, predicting the need for interventions, predicting the aggressiveness of a cancer, etc.), and such terms encompass the evaluation of disease response after the administration of a treatment or therapy to the individual. Example prognoses include likelihood of mortality (e.g., <1%, <5%, <10<, <20%, <30%, <40%, <50%, >50%, >60%, >70%, >80%, >90%, >95%, >99%), likelihood of responsiveness/resistance to treatment (e.g., <1%, <5%, <10<, <20%, <30%, <40%, <50%, >50%, >60%, >70%, >80%, >90%, >95%, >99%), likely lifespan (e.g., <1 month, <2 months, <3 month, <6 months, <1 year, 2 years, 3 years, >3 years, etc.).

"Evaluate", "evaluating", "evaluation", and variations thereof encompass both "diagnosis" and "prognosis" and also encompass determinations or predictions about the future course of a disease or condition in an individual who does not have the disease as well as determinations or predictions regarding the likelihood that a disease or condition will recur in an individual who apparently has been cured of the disease. The term "evaluate" also encompasses assessing an individual's response to a therapy, such as, for example, determining the aggressiveness of a disease or condition, predicting whether an individual is likely to respond favorably to a therapeutic agent or is likely to develop resistance to a therapeutic agent, selecting a therapeutic agent for administration to an individual, or monitoring or determining an individual's response to a therapy that has been administered to the individual.

As used herein, "detecting" or "determining" with respect to a biomarker or biomarker ratio includes the use of both the instrument used (if used) to observe and record a signal corresponding to a biomarker(s), the reagents required to generate that signal, and/or analysis of signals to generate a value or ratio. In various embodiments, a level or ratio is detected using any suitable method, including fluorescence, microscopy, imaging, etc.

As used herein, the term "antibody" refers to a whole antibody molecule or a fragment thereof (e.g., Fab, Fab', F(ab')$_2$, Fv, scFv, Fd, diabodies, and other antibody fragments that retain at least a portion of the variable region of an intact antibody), it may be a polyclonal or monoclonal antibody, a chimeric antibody, a humanized antibody, a human antibody, etc. As used herein, when an antibody or other entity "specifically recognizes" or "specifically binds"

an antigen or epitope, it preferentially recognizes the antigen in a complex mixture of proteins and/or macromolecules, and binds the antigen or epitope with affinity which is substantially higher than to other entities not displaying the antigen or epitope. In this regard, "affinity which is substantially higher" means affinity that is high enough to enable detection of an antigen or epitope which is distinguished from entities using a desired assay or measurement apparatus. Typically, it means binding affinity having a binding constant ($K_a$) of at least $10^7$ $M^{-1}$ (e.g., $>10^7$ $M^{-1}$, $>10^8$ $M^{-1}$, $>10^9$ $M^{-1}$, $>10^{10}$ $M^{-1}$, $>10^{11}$ $M^{-1}$, $>10^{12}$ $M^{-1}$, $>10^{13}$ $M^{-1}$, etc.). In certain such embodiments, an antibody is capable of binding different antigens so long as the different antigens comprise that particular epitope. In certain instances, for example, homologous proteins from different species may comprise the same epitope.

The term "primary antibody" refers to an antibody that binds specifically to the target antigen (e.g., biomarker) in a sample. A primary antibody is often the first antibody used in an assay or diagnostic test.

The term "secondary antibody" refers to an antibody that binds specifically to a primary antibody. A secondary antibody may be labeled with a detection reagent (e.g., fluorescent dye), thereby forming a bridge between the primary antibody and the detection reagent. The secondary antibody is generally the second antibody used in an assay or diagnostic test.

DETAILED DESCRIPTION

Provided herein are methods and systems for the analysis of biomarkers, and methods of providing diagnoses and/or prognoses therewith. In particular, methods and systems for performing biomarker ratio imaging microscopy (BRIM) are provided, as well as methods of using BRIM for the analysis of biomarker pairs (e.g., CD44/CD24, N-cadherin/ E-cadherin, CD74/CD59, etc.) for diagnosis and/or prognosis of cancer (e.g., ductal carcinoma in situ).

Ratio imaging microscopy has been used in calcium, membrane potential, intracellular pH, protein activation, fluorescence polarization, viscosity, proximity, and water permeability studies (refs. 6-10; incorporated by reference in their entireties). Two images are collected during ratio imaging microscopy:one increasing and one decreasing in intensity with the parameter of interest. Either one or two fluorescent labels may be used for ratio determination (refs. 6-16; incorporated by reference in their entireties).

In some embodiments, provided herein are systems and methods utilizing biomarker ratio imaging microscopy (BRIM). During BRIM fluorescence images of two biomarkers are collected at distinct wavelengths wherein the expression of one biomarker increases with tumor aggressiveness while the second decreases with aggressiveness. By dividing the former by the latter, high contrast images linked with tumor aggressiveness are created. Moreover, optical artifacts due to variations in sample thickness disappear. In experiments conducted during development of embodiments herein, ratiometric analysis of exemplary biomarker pairs, the levels of which were determined by fluorescence imaging microscopy, were used to classify potentially cancerous lesions as being linked to either aggressive or non-aggressive cancers. In particular, using BRIM, micrographs of biomarkers whose expression correlates with breast cancer aggressiveness are divided by micrographs of biomarkers whose expression negatively correlates with aggressiveness to create computed micrographs reflecting a relationship to tumor aggressiveness. Exemplary biomarker pairs CD44/ CD24, N-cadherin/E-cadherin, and CD74/CD59 were used to retroactively stratify DCIS biopsy samples. BRIM identified subpopulations of DCIS lesions with ratiometric properties resembling either benign fibroadenoma or invasive carcinoma samples. This work demonstrates the existence of distinct subpopulations of DCIS lesions, which have utility in the providing breast cancer diagnoses and/or prognoses, as well as with other cancers that current methods fail to accurately assess risk for (e.g., prostate cancer).

For example, although screening tools for cervical and colorectal cancer reduced the incidence of advanced forms of these diseases, screening mammography has not yielded a similar reduction in advanced breast cancer (refs. 1-3; incorporated by reference in their entireties). The BRIM experiments conducted during development of embodiments herein using biomarkers of breast cancer aggressiveness have identified DCIS aggressiveness subtypes. These experiments also provide the first robust images of $CD44^{hi}/CD24^{lo}$ cells within human tissue samples. The identification of intraductal $N-cad^{hi}/E-cad^{lo}$ cells indicates that the EMT accompanies human cancer. In some DCIS cases, a sub-population of $CD74^{hi}/CD59^{lo}$ stromal cells can be observed, indicating that stromal cells participate in disease.

In some embodiments, provided herein is a microscopy-based tool (e.g., BRIM) that recognizes tumor cell heterogeneity, and permits biomarker detection at comparatively high concentrations within organelles. In some embodiments, for image ratioing, the signal intensity is linear with respect to biomarker number. In some embodiments, enzyme-linked amplification methods are inappropriate due to their non-linear properties (ref. 29; incorporated by reference in its entirety). Fluorescence microscopy avoids this difficulty. Variations in cell shape, size, and section thickness influence a sample's perceived brightness. These optical path-length artifacts are removed by ratio imaging microscopy (refs. 6, 7; incorporated by reference in their entireties). As instrument-dependent factors are present in the numerator and denominator, they are also removed by image ratioing, thereby improving standardization. Noise due to sample loss during processing, knife chatter during sectioning and others are removed by ratioing (e.g., the upper left corner of FIG. 1 panel A). Hence, BRIM overcomes many drawbacks of conventional histopathology.

In experiments conducted during development of embodiments herein, the association between the low BRIM scores of DCIS and fibroadenoma compared to the high BRIM scores of DCIS and IDC support the clinical relevance of these DCIS subtypes. The ability to stratify DCIS lesions and to identify potentially non-aggressive and aggressive lesions allows clinicians to address overtreatment in breast cancer (e.g., only treating highly or moderately aggressive cancers, not treating unaggressive cancers, differently-treating unaggressive cancers, etc.). In some embodiments, BRIM is integrated into clinical pathology practices. In some embodiments, BRIM is useful in the cytologic study of aspirates in breast cancer and in peritoneal fluids in ovarian cancer. Since over-diagnosis has also been reported for prostate, lung and other cancers (ref 30; incorporated by reference in its entirety), BRIM may be broadly useful in cancer diagnosis, prognosis, and treatment.

Embodiments herein find use in the evaluation of disease in a subject. Ratios of biomarkers (e.g., the levels of which were determined by fluorescence imaging microscopy) are analyzed to determine the presence/absence, aggressiveness, degree of progression, resistance/responsiveness to treatment, etc. of a disease or condition. Particular embodiments find use in the evaluation of cancer in a subject. In some embodiments, the cancer is cancer is selected from the group consisting of acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophilic leukemia, blast cell leukemia, bovine leukemia, chronic myelocytic leukemia, leukemia cutis, embryonal leukemia, eosinophilic leukemia, Gross' leukemia, Rieder cell leukemia, Schilling's leukemia, stem cell leukemia, subleukemic leukemia, undifferentiated cell leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiennoid carcinoma, carcinoma epitheliale adenoides, exophytic carcinoma, carcinoma ex ulcere, carcinoma fibrosum, gelatiniform carcinoma, gelatinous carcinoma, giant cell carcinoma, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, carcinoma villosum, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, naspharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, chondrosarcoma, fibrosarcoma, lymphosarcoma, melanosarcoma, myxosarcoma, osteosarcoma, endometrial sarcoma, stromal sarcoma, Ewing's sarcoma, fascial sarcoma, fibroblastic sarcoma, giant cell sarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, telangiectaltic sarcoma, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, Harding-Passey melanoma, juvenile melanoma, lentigo maligna melanoma, malignant melanoma, acral-lentiginous melanoma, amelanotic melanoma, benign juvenile melanoma, Cloudman's melanoma, S91 melanoma, nodular melanoma subungal melanoma, and superficial spreading melanoma.

In some embodiments, methods and systems herein find use in evaluating/characterizing an already-detected condition in a subject. In some embodiments, a subject has received and initial or partial diagnosis, and embodiments herein are employed to further characterize the condition. In some embodiments, screening of the subject has identified a risk factor, and embodiments herein are employed to provide a more detailed diagnosis. In some embodiments, a subject has been diagnosed with a condition, and embodiments herein are employed to provide a prognosis. In some embodiments, an abnormal condition (e.g. breast lump, DCIS, pre-cancerous lesion, etc.) is detected in a subject, and embodiments herein are employed to characterize the likelihood that the abnormal condition is, or will become invasive, malignant, aggressive, etc.

In some embodiments, a sample from a subject is analyzed by the methods described herein. Depending on the application and/or the disease/condition being evaluated, different samples may be suitable. A sample in accordance with one embodiment of the invention may be solid or fluid. Suitable examples of samples may include, but are not limited to, cultures, blood, plasma, serum, saliva, cerebral spinal fluid, pleural fluid, milk, lymph, sputum, semen, urine, stool, tears, saliva, needle aspirates, external sections of the skin, respiratory, intestinal, and genitourinary tracts, tumors, organs, cell cultures or cell culture constituents, or solid tissue sections. Cell cultures may include mixed cell culture, stem cell colonies or cultures derived from various cancer or primary cell lines. In some embodiments, the sample may be analyzed as is, that is, without harvest and/or isolation of the target of interest. In an alternative embodiment, harvesting and isolation of targets may be performed prior to analysis. In some embodiments, the methods disclosed herein may be particularly suitable for in vitro analysis of samples.

A sample may include any of the aforementioned samples regardless of their physical condition, such as, but not limited to, being frozen or stained or otherwise treated. In some embodiments, a sample may include compounds which are not naturally intermixed with the sample in nature such as preservatives, anticoagulants, buffers, fixatives, nutrients, antibiotics, or the like.

In some embodiments, a sample may include a tissue sample or section, a whole cell, a cell constituent, e.g., cell organelle, a cytospin, or a cell smear. In some embodiments, a sample essentially includes a tissue sample. A tissue sample may include a collection of similar cells obtained from a tissue of a subject that may have a similar function. In some embodiments, a tissue sample may include a collection of similar cells obtained from a tissue of a human. Suitable examples of human tissues include, but are not limited to, epithelium; the connective tissues, including blood vessels, bone and cartilage; muscle tissue; and nerve tissue. The source of the tissue sample may be solid tissue obtained from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. In some embodiments, the tissue sample may include primary or cultured cells or cell lines.

In some embodiments, a sample includes tissue sections from healthy or diseased tissue samples (e.g., tissue section from breast tissue, prostate, colon, etc.). A tissue section may include a single part or piece of a tissue sample, for example, a thin slice of tissue or cells cut from a tissue sample. In some embodiments, multiple sections of tissue samples may be taken and subjected to analysis.

In some embodiments, a sample is obtained by biopsy. Examples include, but are not limited to, fine needle biopsy, needle biopsy, core needle biopsy and surgical biopsy (e.g., brain biopsy), and lavage.

In some embodiments, the levels of one or more pairs of biomarkers in a sample are analyzed by fluorescence imaging microscopy. In such embodiments, an optically-detectable label or imaging agent is associated with the biomarkers (e.g., separately-detectable labels are associated with each biomarker), and the label is detected by imaging techniques.

In some embodiments, antibodies having a label or an imaging agent covalently or noncovalently attached thereto are used to label biomarkers. Suitable imaging agents include, but are not limited to, radionuclides, detectable tags, fluorophores, fluorescent proteins, enzymatic proteins, and the like. In some embodiments, suitable optically-detectable labels are include various chromogenic, fluorogenic, and lumigenic substrates. One of skill in the art will be familiar with suitable methods for attaching imaging agents to antibodies other agents. For example, the imaging agent can be attached via site-specific conjugation. The imaging agent can also be directly attached via non-site specific conjugation, e.g., covalent attachment of the imaging agent to primary amine groups present in the antibody and/or polypeptide. One of skill in the art will appreciate that an imaging agent can also be bound to a protein via noncovalent interactions (e.g., ionic bonds, hydrophobic interactions, hydrogen bonds, Van der Waals forces, dipole-dipole bonds, etc.).

Non-limiting examples of fluorophores or fluorescent dyes suitable for use as imaging agents include Alexa Fluor dyes (Invitrogen Corp.; Carlsbad, Calif.), fluorescein, fluorescein isothiocyanate (FITC), Oregon Green; rhodamine, Texas red, tetrarhodamine isothiocynate (TRITC), CyDye fluors (e.g., Cy2, Cy3, Cy5), and the like.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof. Specific examples of GFP variants include, but are not limited to, enhanced GFP (EGFP), destabilized EGFP, the GFP variants, cerulean fluorescent proteins, and the yellow fluorescent protein. DsRed variants include mStrawberry, mCherry, mOrange, mBanana, mHoneydew, and mTangerine, mRaspberry and mPlum.

Any device, instrument, or method known in the art for imaging, microscopy, and/or detecting (e.g., quantifying) a detectable label (e.g., optically-detectable) is suitable for use in embodiments herein. Methods and devices for detecting an optical response include, without limitation, visual inspection, CCD cameras, video cameras, photographic film, laser-scanning devices, fluorometers, photodiodes, quantum counters, epifluorescence microscopes, confocal microscopes, scanning microscopes, fluorescence readers, or signal amplification using photomultiplier tubes.

EXPERIMENTAL

Methods

Study Design and Patient Samples

BRIM was used to evaluate the co-expression of biomarkers correlating and anti-correlating with breast cancer aggressiveness in a retrospective study of DCIS samples. Fibroadenoma of the breast and invasive ductal carcinoma (IDC) were used to compare with DCIS samples. Formal-fixed paraffin-embedded (FFPE) pathology samples were purchased from the National Disease Research Interchange (NDRI), a National Resource Center (Bethesda, Md.) and the Cooperative Human Tissue Network (CFTN) (Columbus, Ohio; Philadelphia, Pa.; and Nashville, Tenn.). Samples were from mastectomies of females aged 37-96 years after informed consent was obtained from all subjects. The tissues examined in this study were not needed for patient care.

Biomarkers

Biomarkers were selected based upon their relative changes in expression in normal tissue vs. IDC. Although a high dynamic range of intensities is desirable, intensity differences causing division by zero errors are unhelpful. Punctate biomarker images (e.g., ribosomal biomarkers) and biomarkers that translocate between organelles (e.g., gene regulatory proteins) are also unsuitable for ratioing. Experiments conducted during development of embodiments herein focused on the following exemplary biomarker pairs: $CD74^{hi}/CD59^{lo}$, $CD44^{hi}/CD24^{lo}$ and $N\text{-}cad^{hi}/E\text{-}cad^{lo}$, which are plasma membrane proteins.

As antibodies may differ in their titer, epitope recognition, and binding after antigen retrieval, matched antibodies were used in BRIM experiments. The primary antibodies used in these studies were: Ms anti-N-Cadherin (Abcam ab98952), Rb anti-E-Cadherin (Abcam ab15148), Ms anti-CD74 (Abcam ab9514), Rb anti-CD59 (Abcam ab133707), Rb anti-CD44 (Abcam ab41478), Ms anti-CD24 (Biolegend 311102). The secondary antibodies used in this study were: Gt anti-Ms Alexa 488 (Invitrogen A11029) and Dk anti-Rb Alexa 568 (Invitrogen A10042). These antibodies were typically used at a 1/100 dilution.

Histochemistry of Tissue Sections

Sections of paraffin-embedded samples were cut into 5 μm sections. Sections were stained with hematoxylin/eosin (H&E). For immunofluorescence staining, sections were deparaffinized and re-hydrated by sequential incubation in a graded ethanol series. After rehydration in PBS, sections were subjected to heat-mediated antigen retrieval in 10 mM citric acid buffer, pH 6.0. Sections were blocked using an endogenous biotin blocking kit for 30 min., and then blocked with blocking solution (10% normal goat serum/6%

BSA in PBS) for 1.5 hr. at room temperature. After blocking procedures, sections were incubated with 2 µg/mL of antibody diluted in 1% BSA in PBS overnight at 4° C. Sections were washed with PBS then incubated with 10 µg/mL biotin-XX goat anti-mouse IgG diluted in 1% BSA in PBS for 2 hr at room temperature. After incubation, the sections were washed with PBS. Finally, the sections were incubated with fluorescently labeled secondary antibody for 1.5 hr., washed with PBS, and then mounted in 90% glycerol in PBS. The H&E and immunofluorescence images were acquired from serial sections from each block.

Optical Microscopy

Fluorescence microscopy was performed using a Nikon TE2000-U inverted microscope (Nikon, Melville, N.Y.) and an Andor iXon camera (Andor Technology, Belfast, Northern Ireland) with a 100 W mercury lamp. Ratio imaging experiments were performed (refs. 13, 14; incorporated by reference in their entireties). To avoid cross-talk between the emission wavelengths of the fluorescent tags, band-pass filters with the "sharpest" cut-offs and greatest out-of-band reflectances were used (Chroma ET-fluorescein filter set (#49011) and Chroma ET-Cy3/rhodamine filter set (#49004) (Chroma Tech. Corp., Bella Falls, Vt.)). These zero pixel shift optics were chosen for their high performance in ratio imaging. For most experiments, 20 images, each acquired for 0.2 sec., were averaged. The electron multiplying charge coupled device chip was cooled to −85° C. Typical camera settings were: multiplication gain, 150; vertical shift speed, 3.04 msec./pixel and 14-bit digitization at 10 MHz. Images were captured with Metamorph and processed with MetaFluor software (Molecular Devices, Downingtown, Pa.) to calculate image ratios. Micrographs were evaluated using ImageJ software. Segmentation was performed with the ISODATA (iterative self-organizing data analysis) technique. A local implementation of the Otsu algorithm (ref 31; incorporated by reference in its entirety) was used for comparison. Ratiometric images at a gray value of ≥130 were quantified by counting the number particles five or more pixels in size. The highest BRIM value from each patient's micrographs was plotted. Several micrographs from each patient sample were analyzed because some micrographs contained lower numbers of cells, for example, due to an abundance of fatty tissue. Data were displayed using two-dimensional (KaleidaGraph, Synergy Software, Reading, Pa.) or three-dimensional (Plotly, Montreal, Quebec, CA) graphing software.

Statistics

In vitro data are presented as the mean±sd to describe the dispersion of the data. Data were evaluated with Student's t-test. Welch's t-test, which is less susceptible to departures from a normal distribution, yielded indistinguishable results.

Results

Using BRIM, $CD44^{hi}/CD24^{lo}$ cells were localized in DCIS pathology samples. CD44 and CD24 are cell surface adhesive proteins participating in proliferation and differentiation (ref 17; incorporated by reference in its entirety). $CD44^{hi}/CD24^{lo}$ cells have been reported to represent a population of breast cancer stem cells (ref 18; incorporated by reference in its entirety), which were visualized by ratioing CD44 (numerator image) against CD24 (denominator image). FIG. 1A-C shows: CD44, CD24, and $CD44^{hi}/CD24^{lo}$ images, respectively. The presence of high ratio cells in the ducts is depicted in FIG. 1C and FIG. 4D. Quantitative line profile analyses of FIG. 1A-C are shown in panels D-F, respectively. These data illustrate the improvements provided by BRIM. For example, note that the parallel increases in CD44 and CD24 intensity seen in the region labeled "high noise" in FIGS. 1D and E cancel out during ratioing, thus highlighting $CD44^{hi}/CD24^{lo}$ cells. However, $CD44^{hi}/CD24^{lo}$ cells could not be observed in a sub-population DCIS samples (see below).

Figure 2:
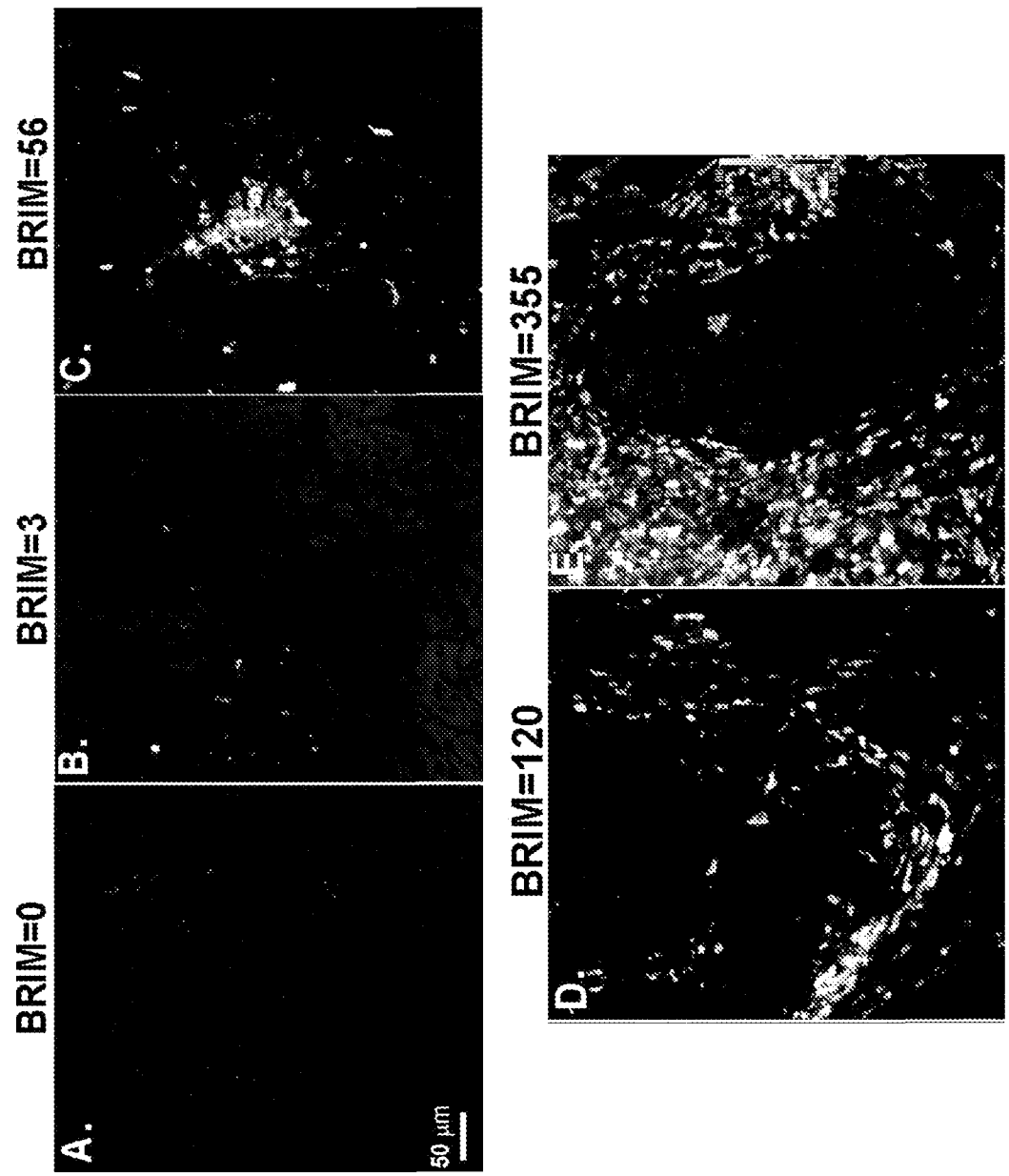
FIG. 2. Stratification of DCIS samples using tissue sections stained with anti-CD74 and anti-CD59. A broad range of stromal cell ratio values were observed for samples from DCIS patients (panels A-E). To quantify these data, further image processing was performed. The ratio of each pixel in a sample of normal tissue is shown in the white plot of panel F whereas an identical plot of DCIS tissue is shown as black in this panel. This diagram shows that gray values of ≥130 (see arrow) are only found in the DCIS sample. Panel G shows pixels with gray values of ≥130, which confirms that stromal cells account for high BRIM values. The ascending Pareto plots of panels H-J show electronic counts of $CD74^{hi}/CD59^{lo}$ particles (ordinate) versus the data point index (abscissa). Each dot represents the BRIM score of one patient. Samples from simple fibroadenoma patients (H) display little or no signals (N=16). DCIS samples (I) segregate into two populations: those scoring near the level of fibroadenomas and those samples scoring highly for the biomarker ratio pair (N=23). High levels of statistical significance (P<0.0001) are seen in comparing the low BRIM with high BRIM samples. The high BRIM scores can be seen for the DCIS population and IDC patient samples (J) (N=26). Quantitative BRIM counts are shown at the top of panels A-E. A ratio scale is given on the far right of panel E. (20× objective)
Figure 2:
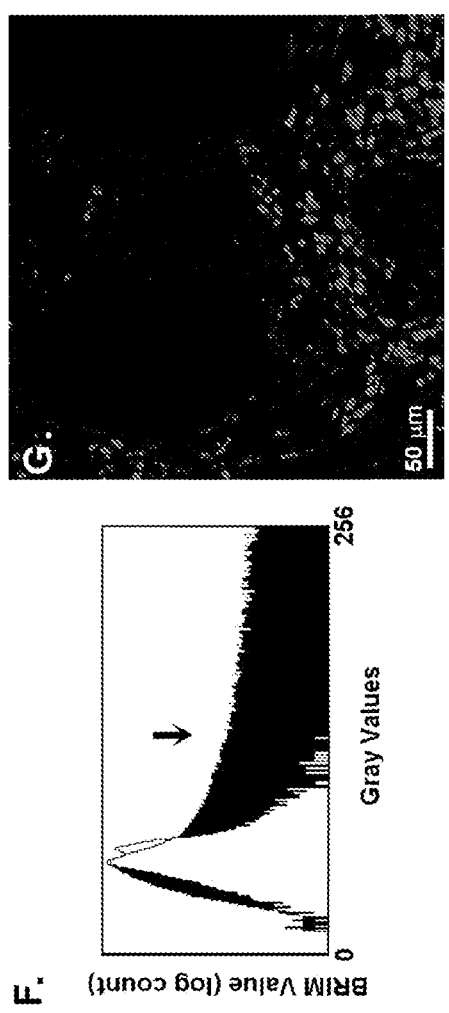
Figure 2:
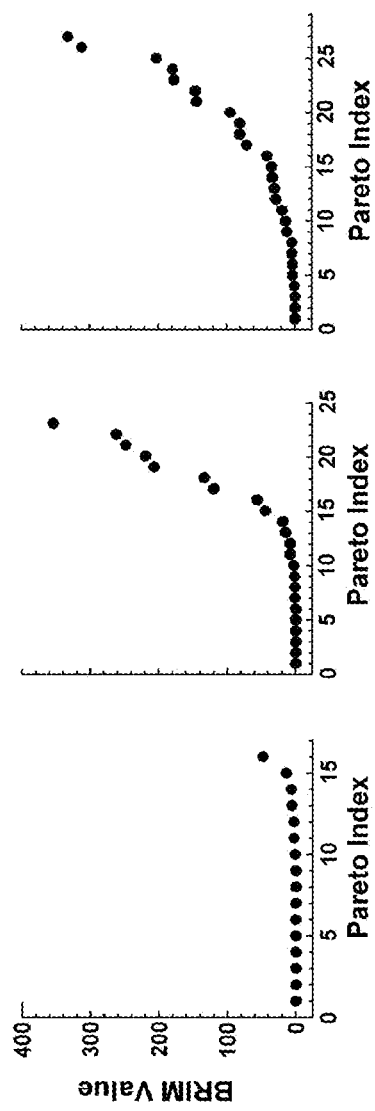
Figure 4:
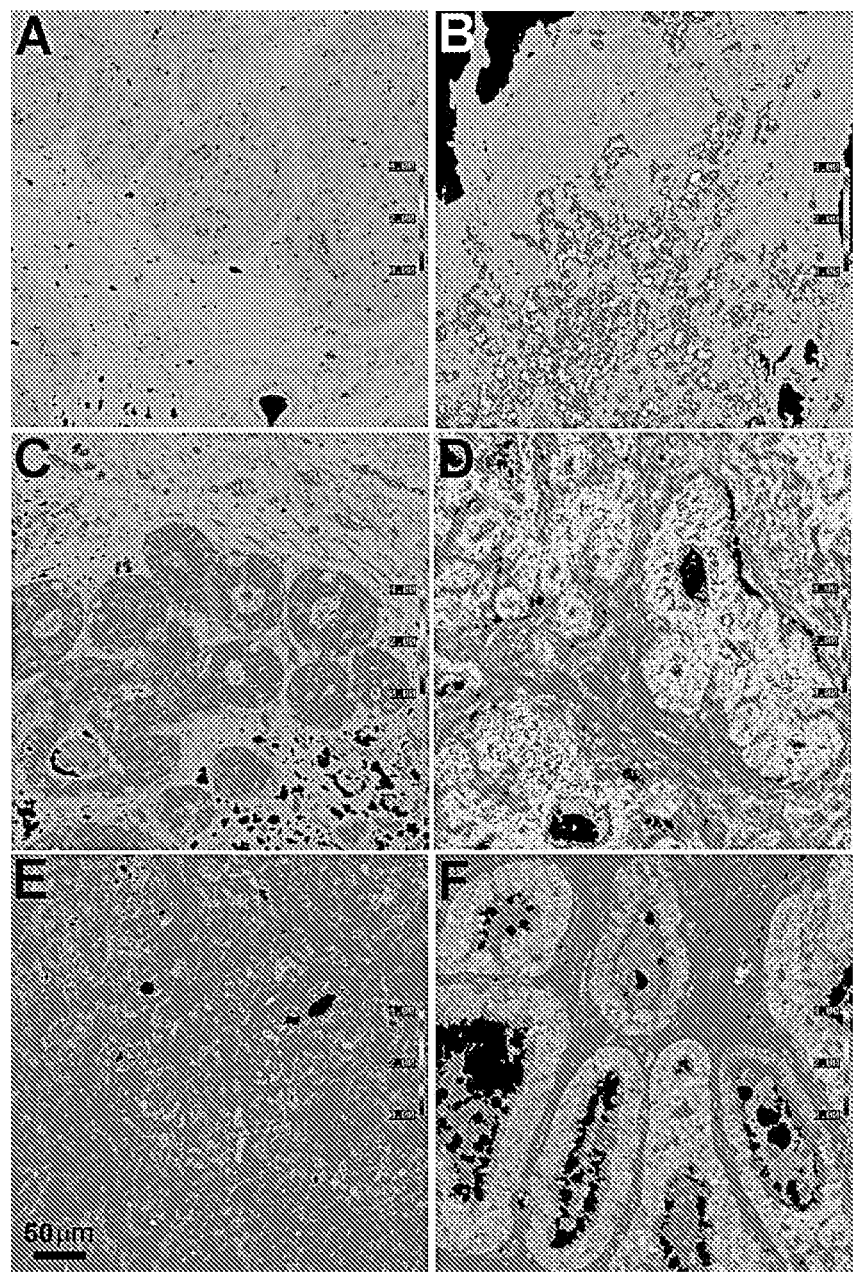
FIG. 4. Examples of pseudocolor ratio images of DCIS tissue samples are shown. This figure illustrates DCIS tissue samples with low (A, C, E) and high (B, D, and F) image ratios for the biomarkers: CD74/CD59 (A, B), CD44/CD24 (C, D), and N-cadherin/E-cadherin (E, F). Stromal and epithelial cells are positive in panels B and D, respectively. Ratio bars are given along the right hand side of each figure.
Figure 5:
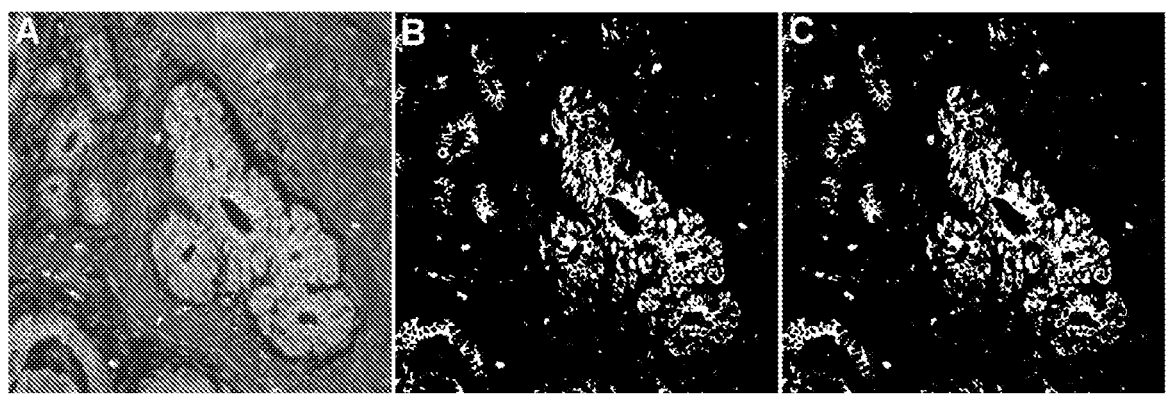
FIG. 5. Examples of image segmentation producures are shown. A ratiometric N-cadherin/E-cadherin image of a DCIS sample is shown (panel A). In panel B, the ratio image of panel A was segmented using the ISODATA algorithm. Panel C shows the same image segmented using the Otsu algorithm. The threshold was interactively selected by comparison with normal and simple fibroadenoma samples in panel B whereas in threshold was automatically optimized in panel C.
Figure 6:
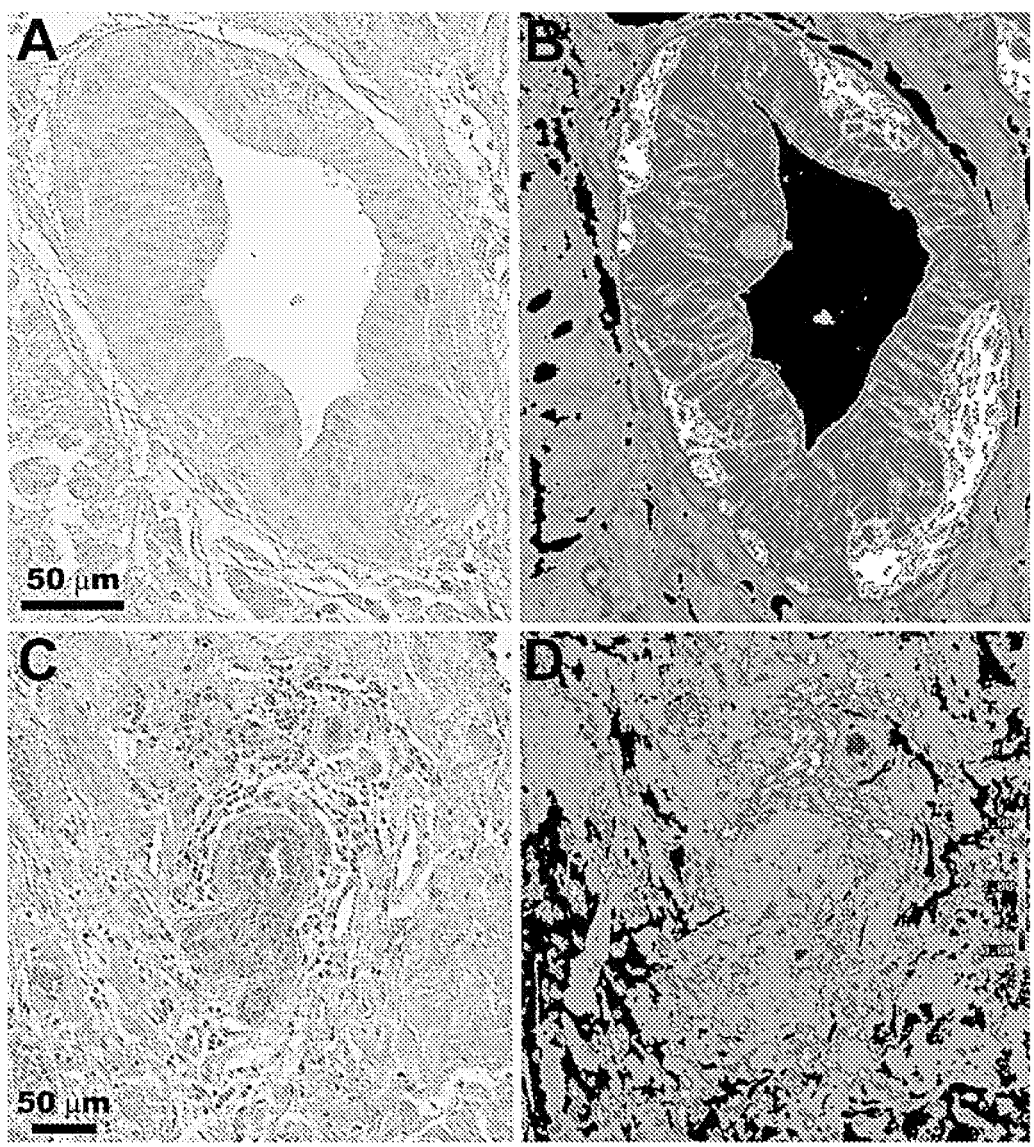
FIG. 6. High BRIM ratios are found for IDCs. H&E (A, C) and BRIM (B, D) micrographs of tissue sections of an IDC. In each pair of micrographs, images of the same tissue region for two nearby tissue sections are shown. An H&E stain of an IDC tissue sample is illustrated in panel A. Panel B shows the same region stained for CD44 and CD24 after BRIM processing. The highest BRIM ratio cells at the perimeter of the duct do not have a columnar morphology. Panels C shows an H&E stain of an IDC sample. Panel D shows a serial section of the same patient sample stained with CD74 and CD59 then processed. $CD74/CD59^{lo}$ cells are apparent. A, C; bar=50 mm.

Overexpression of CD74, the HLA class II γ chain, and underexpression of CD59, a complement regulatory protein, are linked to poor patient outcomes (refs. 20, 21; incorporated by reference in their entireties). FIG. 2A-E shows the widely varying ratiometric intensities of five DCIS samples labeled for CD74 and CD59 biomarkers. Micrographs were next quantified for statistical purposes. First pixel intensity histograms of control breast tissue (white region; low BRIM value) were compared with DCIS tissue expressing aggressive biomarker properties (black region; high BRIM value); gray values ≥130 were only found in the DCIS sample (FIG. 2F). FIG. 2G shows an image wherein gray values ≥130 were labeled, which shows that stromal cells, not intraductal cells (FIG. 1C) were labeled. This threshold, based upon differences in clinical breast tissue samples, was applied in subsequent analyses. The results of this segmentation procedure were nearly indistinguishable from that obtained using a non-interactive Otsu algorithm (FIG. 4). FIG. 2I shows the number of high BRIM value particles per 20× micrograph for each DCIS patient. The inflection point found in the Pareto plot of panel I suggests two sample populations with mean particle counts of 4±6 and 190±100, which is further supported by Ashmann's bimodality test (ref 22; incorporated by reference in its entirety). These two populations were distinguishable at a high level of statistical significance ($P<0.0001$). Quantitative data from simple fibroadenoma (5±12) and IDC (76±94) samples are shown as biological reference standards of benign and invasive breast neoplasms (FIGS. 2H and J). These experiments conducted during development of embodiments herein demonstrate that BRIM stratifies DCIS samples. The IDC plot (FIG. 2J) was similar to DCIS samples (FIG. 2I). BRIM micrographs illustrating IDC staining are shown in FIG. 6. The low BRIM DCIS subtype resembles the ratiometric biomarker properties of fibroadenoma samples whereas the high BRIM DCIS subtype more closely resembles IDC samples.

Figure 3:
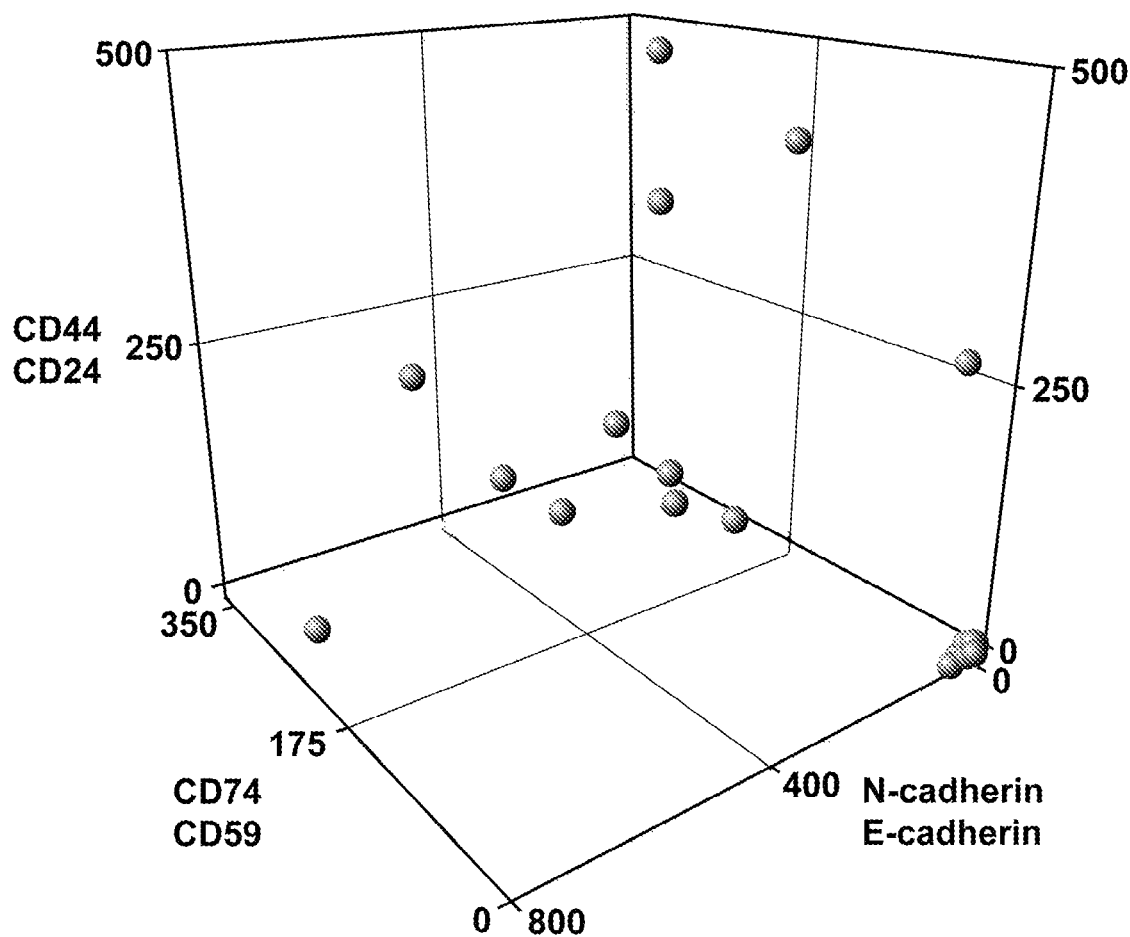
FIG. 3. A three-dimensional rendering of all BRIM data for DCIS patients. Values of the parameters $CD74^{hi}/CD59$ (z axis), CD44/CD24 (x axis) and N-cadherin/E-cadherin (y axis) are plotted for each DCIS patient. Some samples (18) had BRIM values far from the origin (0, 0, 0). Of the samples near the origin, 5 had scores of <50 for CD74/CD59 and 0-2 for the other two parameters. Note that DCIS samples near the walls of the three-dimensional plot could be interpreted as false-negatives if only one BRIM parameter was measured.
Figure 7:
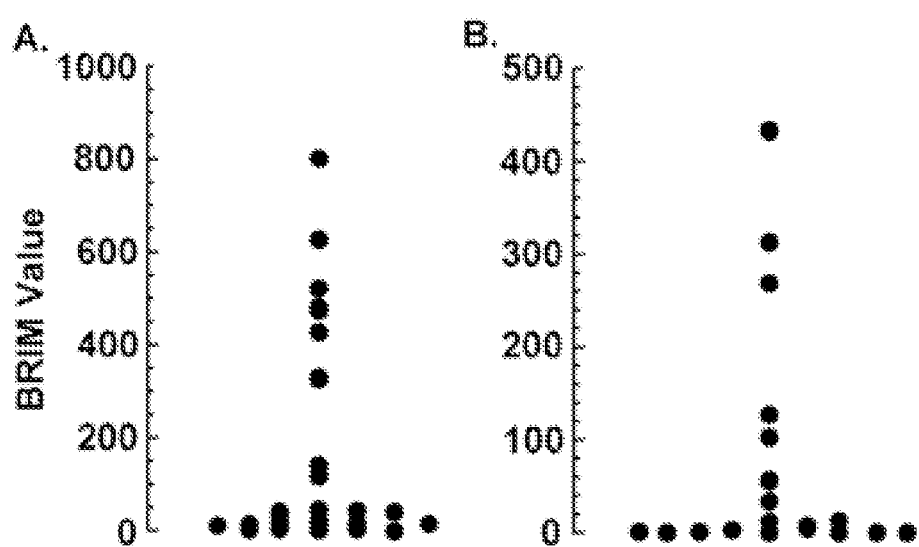
FIG. 7. Stratification of DCIS samples using N-cadherin/E-cadherin (A) and CD44/CD24 (B) ratiometric images are shown. Each dot represents the BRIM value of one patient. A group of patients had very low BRIM values, thus accounting for the extensive number of cases near the baseline. Data points may overlap.

As DCIS lesions may become aggressive independently of stromal cell phenotype, and to demonstrate stratification by other biomarker pairs, additional biomarkers were analyzed. As the endothelial-mesenchymal transition (EMT) is believed to participate in metastasis (ref 23; incorporated by reference in its entirety), we quantified $N\text{-}cadherin^{hi}/E\text{-}cadherin^{lo}$ labeling. Similarly, $CD44^{hi}/CD24^{lo}$ cells also contribute to aggressiveness (ref 18; incorporated by reference in its entirety). $CD44^{hi}/CD24^{lo}$ and $N\text{-}cad^{hi}/E\text{-}cad^{lo}$ cells were found to stratify DCIS tissues lesions (FIG. 7). FIG. 3 shows a three dimensional plot of $CD74^{hi}/CD59^{lo}$, $CD44^{hi}/CD24^{lo}$ and $N\text{-}cad^{hi}/E\text{-}cad^{lo}$ BRIM findings for each patient. This plot reveals a low BRIM DCIS sub-population near the origin (0, 0, 0) and a second subtype far from the origin. The average age of patients whose samples had low BRIM scores (50 yrs) was significantly ($P<0.05$) less than those with high BRIM scores (64 yrs.) (Table 1), which is consistent with recent studies (ref. 24; incorporated by reference in its entirety). Within this dataset, 5 samples (22%) had scores of 0-2 for $CD74^{hi}/CD59^{lo}$ and CD44/CD24 as well as <50 for $N\text{-}cad^{hi}/E\text{-}cad^{lo}$ (this higher score corrects for $N\text{-}cad^{hi}/E\text{-}cad^{lo}$ stromal cells), indicating a low level of aggressive biomarker labeling.

TABLE 1

DCIS Patient Details

| number | age | CD74/ CD59 | N-cad/ E-cad[1] | CD44/ CD24 | architecture | grade | Antigen status[2] | BRIM status |
|---|---|---|---|---|---|---|---|---|
| 1 | 50 | 263 | 117 | 486 | comedo, cribriform, micropapillary | high | na | high |
| 2 | 53 | 56 | 474 | 194 | cribriform | intermediate | na | high |
| 3 | 67 | 220 | 627 | 248 | cribriform, solid | intermediate | na | high |
| 4 | 44 | 3 | 481 | 211 | solid | Low to intermediate | na | high |
| 5 | 48 | 1 | 17 | 8 | solid, cribriform, comedo | high | ER+, PR+ | high |
| 6 | 54 | 207 | 802 | 55 | comedo | high | ER− | high |
| 7 | 46 | 120 | 140 | 432 | solid, micropapillary mucinous | low | na | high |
| 8 | 82 | 249 | 330 | 57 | comedo, cribriform, micropapillary | high | ER+, PR+ | high |
| 9 | 52 | 0 | 31 | 9 | solid, cribriform | high | ER+, PR− | high |
| 10 | 64 | 44 | 522 | 434 | cribriform, papillary | intermediate | ER+, PR+ | high |
| 11 | 59 | 134 | 326 | 313 | comedo | high | ER− | high |
| 12 | 56 | 355 | 41 | 55 | solid, comedo | intermediate to high | na | high |
| 13 | 55 | 1 | 11 | 4 | solid, cribriform | low | na | high |
| 14 | 79 | 8 | 13 | 13 | comedo | high | na | high |
| 15 | 42 | 0 | 0 | 12 | cribriform, papillary, solid, focal apocrine features | intermediate | na | high |
| 16 | 38 | 15 | 15 | 34 | Comedo, cribriform apocrine features | high | na | high |
| 17 | 37 | 19 | 42 | 127 | micropapillary | low | na | high |
| 18 | 46 | 8 | 20 | 5 | comedo, cribriform, solid | high | na | high |
| 19 | 52 | 0 | 1 | 1 | cribriform solid | intermediate | na | low |
| 20 | 50 | 0 | 1 | 0 | solid, cribriform | high | na | low |
| 21 | 53 | 0 | 0 | 1 | cribriform, micropapillary | intermediate | na | low |
| 22 | 51 | 0 | 14 | 0 | cribriform, solid | high | na | low |
| 23 | 43 | 2 | 13 | 0 | solid, cribriform | high | na | low |

1) N-cad$^{hi}$/E-cad$^{lo}$ cells may be both stromal cells and tumor cells. Thus, some background level of positivity is expected. Intraductal N-cad$^{hi}$/E-cad$^{lo}$ cells and BRIM values >50 indicate an aggressive phenotype.
2) na = not available.

Figure 8:
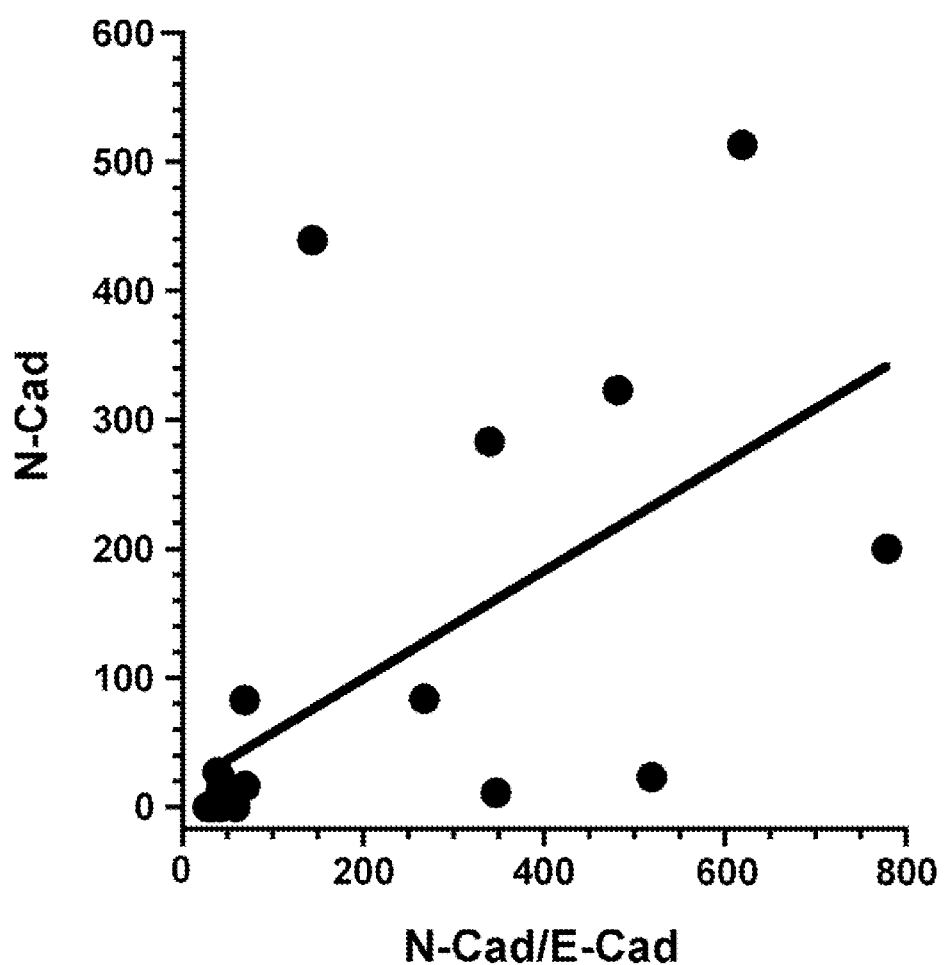
FIG. 8. Comparison of N-cadherin/E-cadherin ratiometric results (abscissa) with single channel assessments of N-cadherin (ordinate) of DCIS samples. The N-cad and N-cad/E-cad results are from matched sets. The correlation coefficient (R=0.61) indicates that these two measures weakly correlate. This weak correlation underscores the difference between conventional imaging and BRIM. This plot also reveals that some cells with low N-cadherin levels nevertheless expressed high N-cadherin/E-cadherin ratios.

To illustrate the advantages of BRIM over conventional fluorescence imaging, BRIM results were compared with matched conventional fluorescence micrographs of numerator images. FIG. 8 shows quantitative DCIS results comparing particle counts of N-cadherin images with particle counts of matched N-cad$^{hi}$/E-cad$^{lo}$ images. Although some level of correlation is expected because N-cad images are incorporated in N-cad$^{hi}$/E-cad$^{lo}$ images, statistical analysis indicates that these two measures only weakly correlate (R=0.61). BRIM findings of N-cad$^{hi}$/E-cad$^{lo}$ cells substantially differ from those of conventional fluorescence microscopy (N-cad$^{hi}$ cells).

Similarly, weak correlations were observed for comparisons of CD44 versus CD44$^{hi}$/CD24$^{lo}$ (R=0.76) and CD74 versus CD74$^{h1}$/CD59$^{lo}$ (R=0.76). These experiments conducted during development of embodiments herein indicate that analysis of a single biomarker is insufficient to provide reliable prognostic information, and that multi-dimensional BRIM is useful in overcoming these limitations.

REFERENCES

The following references, some of which are cited above by number, are incorporated by reference in their entireties.

1. Bleyer, A. & Welch, H. G. Effect of three decades of screening mammography on breast-cancer incidence. *N. Engl. J Med.* 367, 1998-2005 (2012).
2. Ozanne, E. M., et al. Characterizing the impact of 25 years of DCIS treatment. *Breast Cancer Res. Treat.* 129, 165-73 (2011).

3. Harding, C., et al. Breast cancer screening, incidence, and mortality across US counties. *JAMA Intern. Med.* 175, 1483-1489 (2015).
4. Marshall, E. Breast cancer. Dare to do less. *Science* 343, 1454-6 (2014).
5. Esserman, L. J., Thompson, I. M. & Reid, B. Overdiagnosis and overtreatment in cancer: An opportunity for improvement. *JAMA* 310, 797-8 (2013).
6. Bright, G. R., Fisher, G. W., Rogowska, J. & Taylor, D. L. Fluorescence ratio imaging microscopy. *Methods Cell Biol.* 30, 157-92 (1989).
7. Petty, H. R. Fluorescence microscopy: established and emerging methods, experimental strategies, and applications in immunology. *Microsc. Res. Tech.* 70, 687-709 (2007).
8. Doná, E., et al. Directional tissue migration through a self-generated chemokine gradient. *Nature.* 503, 285-9 (2013).
9. Axelrod, D. Fluorescence polarization microscopy. *Methods Cell Biol.* 30, 333-352 (1989).
10. Nalbant, P., Hodgson, L., Kraynov, V., Toutchkine, A., & Hahn, K. M. Activation of endogenous Cdc42 visualized in living cells. *Science.* 305,1615-9 (2004).
12. Floto, R. A., Mahaut-Smith, M. P., Somasundaram, B. & Allen, J. M. IgG-induced $Ca^{2+}$ oscillations in differentiated U937 cells; a study using laser scanning confocal microscopy and co-loaded fluo-3 and fura-red fluorescent probes. *Cell Calcium* 18, 377-89 (1995).
13. Clark, A. J., Diamond, M., Elfline, M. & Petty, H. R. Calicum microdomains form within neutrophils at the neutrophil-tumor cell synapse: role in antibody-dependent target cell apoptosis. *Cancer Immunol. Immunother.* 59, 149-59 (2010).
14. Clark, A. J. & Petty, H. R. Observation of calcium microdomains at the uropod of living morphologically polarized human neutrophils using flash lamp-based fluorescence microscopy. *Cytometry A* 73, 673-8 (2008).
15. Wei, C., et al. Calcium flickers steer cell migration. *Nature.* 457, 901-5 (2009).
16. Gomez, T. M., Robles, E., Poo, M. & Spitzer, N. C. Filopodial calcium transients promote substrate-dependent growth cone turning. *Science.* 291, 1983-7 (2001).
17. Herrera-Gayol, A. & Jothy, S. Adhesion proteins in the biology of breast cancer: contribution of CD44. *Exp. Mol. Pathol.* 66,149-56 (1999).
18. Al-Hajj, M., Wicha, M. S., Benito-Hernandez, A., Morrison, S. J. & Clarke, M. F. Prospective identification of tumorigenic breast cancer cells. *Proc. Natl Acad. Sci. USA.* 100, 3983-8 (2003).
19. Porter, D., et al. Molecular markers in ductal carcinoma in situ of the breast. *Mol. Cancer Res.* 1, 362-75 (2003).
20. Metodieva, G., et al. CD74-dependent deregulation of the tumor suppressor scribble in human epithelial and breast cancer cells. *Neoplasia* 15, 660-8 (2013).
21. Madjd, Z., et al. Loss of CD59 expression in breast tumours correlates with poor survival. *J. Pathol.* 200, 633-9 (2003).
22. Ashman, K. M., Bird, C. M. & Zepf, S. E. Detecting bimodality in astronomical datasets. *Astronomical J.* 108, 2348-2361 (1994).
23. Singh, A. & Settleman, J. EMT, cancer stem cells and drug resistance: an emerging axis of evil in the war on cancer. *Oncogene* 29, 4741-4751 (2010).
24. Weigel, S., et al. Digital Mammography screening: Does age influence the detection rates of low-, intermediate-, and high-grade ductal carcinoma in situ? *Radiology.* 278, 707-713 (2016).
25. Li, X., et al. Intrinsic resistance of tumorigenic breast cancer cells to chemotherapy. *J. Natl. Cancer Inst.* 100, 672-9 (2008).
26. Ledford, H. Cancer theory faces doubts. *Nature* 472, 273-4 (2011).
27. Bhowmick, N. A., Neilson, E. G. & Moses H. L. Stromal fibroblasts in cancer initiation and progression. *Nature* 432, 332-337 (2004).
28. Orimo, A. & Weinberg, R. A. Stromal fibroblasts in cancer: A novel tumor-promoting cell type. *Cell Cycle* 5, 1597-1601 (2006).
29. Exbrayat, J-M, ed. *Histochemical and Cytochemical Methods of Visualization*. CRC Press, Boca Raton, Fla., pa. 299 (2013).
30. Moynihan, R., Doust, J. & Henry, D. Preventing over-diagnosis: how to stop harming the healthy. *BMJ* 344, e3502; DOI:10.1136/bmj.e3502 (2012).
31. Otsu, N. A threshold selection method from gray-level histograms. *IEEE Trans. Sys. Man. Cyber.* 9, 62-66 (1979).

The invention claimed is:
1. A method of evaluating a condition of a subject by biomarker ratio imaging microscopy comprising:
  (a) preparing a sample from the subject by:
    (i) labeling a first biomarker that is positively-correlated with the condition with a first fluorophore, and
    (ii) labeling a second biomarker that is negatively-correlated with the condition with a second fluorophore;
  (b) obtaining a first fluorescence micrograph of the sample by quantitating the first biomarker using fluorescence imaging microscopy;
  (c) obtaining a second fluorescence micrograph of the sample by quantitating the second biomarker using fluorescence imaging microscopy;
  (d) calculating numerical ratios for each corresponding pair of pixels in the first fluorescence micrograph and the second fluorescence micrograph;
  (e) creating a computed micrograph that reflects the numerical ratios; and
  (f) evaluating the condition in the subject based on the computed micrograph.
2. The method of claim 1, wherein the subject previously tested positive for an abnormality, pre-cancer, or cancer during a screening.
3. The method of claim 2, wherein the subject has tested positive for ductal carcinoma in situ (DCIS) and the condition being evaluated is invasive ductal carcinoma.
4. The method of claim 1, wherein the condition is cancer and the first biomarker is CD44 and the second biomarker is CD24.
5. The method of claim 1, wherein the condition is cancer and the first biomarker is CD74 and the second biomarker is CD59.
6. The method of claim 1, wherein the condition is cancer and the first biomarker is N-cadherin and the second biomarker is E-cadherin.
7. The method of claim 1, wherein the labeling comprises contacting the sample with fluorescent dyes conjugated to antibodies or antibody fragments.
8. The method of claim 7, wherein the labeling comprises contacting the sample with primary antibodies that separately bind to the first and second biomarkers, and contacting the sample with fluorescently-labeled secondary antibodies that bind to the primary antibodies.

9. The method of claim 7, wherein the labeling comprises contacting the sample with fluorescently-labelled antibodies that separately bind to the first and second biomarkers.

10. A method of performing biomarker ratio imaging microscopy, comprising:
   (a) obtaining a first fluorescence micrograph of a sample from a subject by quantitating a first fluorescently-labeled biomarker that is positively-correlated with a condition using fluorescence imaging microscopy;
   (b) obtaining a second fluorescence micrograph of the sample by quantitating a second fluorescently-labeled biomarker that is negatively-correlated with a condition using fluorescence imaging microscopy; and
   (c) calculating numerical ratios for each corresponding pair of pixels in the first fluorescence micrograph and the second fluorescence micrograph; and
   (d) creating a computed micrograph that reflects the numerical ratios.

11. The method of claim 10, wherein the condition is cancer and the first biomarker is CD44 and the second biomarker is CD24.

12. The method of claim 10, wherein the condition is cancer and the first biomarker is CD74 and the second biomarker is CD59.

13. The method of claim 10, wherein the condition is cancer and the first biomarker is N-cadherin and the second biomarker is E-cadherin.

14. The method of claim 10, wherein the labeling comprises contacting the sample with fluorescent dyes conjugated to antibodies or antibody fragments.

15. The method of claim 14, wherein the labeling comprises contacting the sample with primary antibodies that separately bind to the first and second biomarkers, and contacting the sample with fluorescently-labeled secondary antibodies that bind to the primary antibodies.

16. The method of claim 14, wherein the labeling comprises contacting the sample with fluorescently-labelled antibodies that separately bind to the first and second biomarkers.

* * * * *